United States Patent [19]

Gerow

[11] 4,175,554
[45] Nov. 27, 1979

[54] PROSTHESIS OF MALE IMPOTENCE

[76] Inventor: Frank J. Gerow, 1200 Moursund, Room 186, Houston, Tex. 77030

[21] Appl. No.: 887,224

[22] Filed: Mar. 16, 1978

[51] Int. Cl.² .............................................. A61F 5/00
[52] U.S. Cl. ...................................................... 128/79
[58] Field of Search .......................................... 128/79

[56] References Cited

U.S. PATENT DOCUMENTS

| | | | |
|---|---|---|---|
| 844,798 | 2/1907 | Hawley | 128/79 |
| 1,153,072 | 9/1915 | Hart | 128/79 |
| 1,270,880 | 7/1918 | Scheinkman | 128/79 |
| 1,362,398 | 12/1920 | Crawford et al. | 128/79 |
| 1,383,944 | 7/1921 | Hart | 128/79 |
| 1,511,572 | 10/1924 | Marshall | 128/79 |
| 1,585,861 | 5/1926 | Huff | 128/79 |
| 2,868,192 | 1/1959 | Dannen | 128/79 |
| 2,899,957 | 8/1959 | Briggs | 128/79 |
| 3,131,691 | 5/1964 | Scott | 128/79 |
| 3,401,687 | 9/1968 | Hood | 128/79 |
| 3,421,504 | 1/1969 | Gibbons | 128/79 |
| 3,446,206 | 5/1969 | De Lano | 128/79 |
| 3,455,301 | 7/1969 | Clark | 128/79 |
| 3,461,863 | 8/1969 | Sullinger | 128/79 |
| 3,495,588 | 2/1970 | Walters | 128/79 |
| 3,495,589 | 2/1970 | Clement | 128/79 |
| 3,511,230 | 5/1970 | Strong | 128/79 |
| 3,612,047 | 10/1971 | Nesbit | 128/79 |
| 3,621,840 | 11/1971 | Macchioni | 128/79 |
| 3,636,948 | 1/1972 | Atchley | 128/79 |
| 3,683,901 | 8/1972 | Wegener | 128/79 |
| 3,759,253 | 9/1973 | Cray | 128/79 |
| 3,832,996 | 9/1974 | Kalnberz | 128/79 |
| 3,845,760 | 11/1974 | Birman | 128/79 |
| 3,853,122 | 12/1974 | Strauch et al. | 128/79 |
| 3,893,456 | 7/1975 | Small et al. | 128/79 |
| 3,920,007 | 11/1975 | Line | 128/79 |
| 3,939,827 | 2/1976 | Brunstetter | 128/79 |
| 3,954,102 | 5/1976 | Buuck | 128/79 |
| 3,982,530 | 9/1976 | Storch | 128/79 |
| 3,987,789 | 10/1976 | Timm et al. | 128/79 |
| 3,991,752 | 11/1976 | Gerow | 128/79 |
| 4,009,711 | 3/1977 | Uson | 128/79 |
| 4,022,196 | 5/1977 | Clinton | 128/79 |

FOREIGN PATENT DOCUMENTS

| | | | |
|---|---|---|---|
| 145821 | 5/1936 | Austria | 128/79 |
| 254211 | 11/1912 | Fed. Rep. of Germany | 128/79 |
| 413258 | 5/1925 | Fed. Rep. of Germany | 128/79 |
| 641684 | 2/1937 | Fed. Rep. of Germany | 128/79 |
| 875853 | 5/1953 | Fed. Rep. of Germany | 128/79 |
| 2606869 | 9/1977 | Fed. Rep. of Germany | 128/79 |
| 336941 | 4/1959 | Switzerland | 128/79 |
| 263377 | 12/1926 | United Kingdom | 128/79 |

*Primary Examiner*—Lawrence W. Trapp
*Attorney, Agent, or Firm*—Darryl M. Springs

[57] ABSTRACT

A device for receiving and positioning in a simulation of an erection the genital organ of an impotent male, which device comprises a sleeve-like body enclosed at one end and having the other end open for receiving the extremity of the male organ. After the organ is inserted, means is provided for introducing a negative pressure on the interior of the body which has the effect of drawing the male organ into the interior of the sleeve in an erection-like position.

12 Claims, 10 Drawing Figures

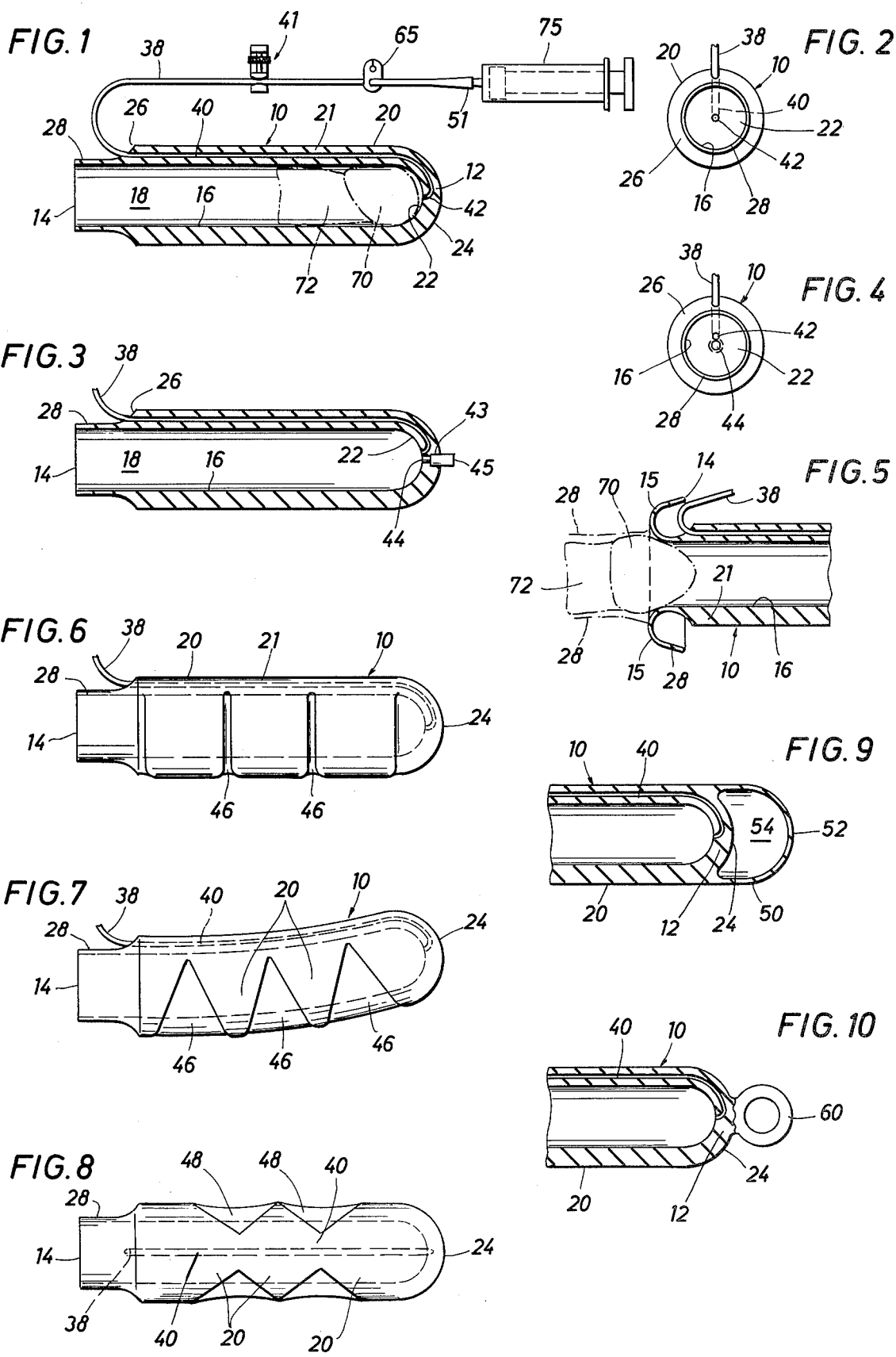

PROSTHESIS OF MALE IMPOTENCE

BACKGROUND OF THE INVENTION

1. Field of the Invention

The present invention relates to a device for receiving the genital organ of a totally impotent male and positioning it in a simulation of an erection for facilitating sexual intercourse.

2. Description of the Prior Art

In the prior art, various solutions have been attempted to aid impotent males in producing or simulating an erection. One such solution is directed to the teaching that pressure applied in various ways at the base of the penis will obstruct venous return from that organ and thereby facilitate or enhance penile erection. These methods are potentially dangerous or harmful as the pressure can injure vessel walls, the walls of the corpora cavernosum and the urethra, possibly risking the viability of the tissues of the penis.

Other prior art methods teach the use of splint-type devices, with open sides and longitudinally running stiff members usually covered with a rubber sleeve to facilitate erection of the male organ and the ability of the user to penetrate during sexual intercourse. However, if the male is impotent and unable to achieve an erection, the splint device cannot be attached to the penis. Further, the loose skin of the penis has a certain tendency to wrap around the edge of the longitudinal member, which in turn then has an irritating sawing action on the skin. The pinching of the skin is painful and the sawing action can be injurious to the skin.

Still another method used in the prior art teaches use of at least a single longitudinal member with circumferential loops positioned to receive and hold the penis in an erect state. At least one of the devices positions a loop directly behind and against the glans penis in the corona, and if tight enough to hold the penis at length, can produce harm to the underlying skin and to the glans, and if loose enough to avoid this injury, will allow the glans to simply slip through the loop. As mentioned above, if the penis cannot achieve any erection, this device cannot be attached. Additionally, some of the supporting circumferential bands are split longitudinally, ostensibly to permit adjustable, snug application to the penis. These longitudinal slits can trap or pinch the skin of the penis, causing injury to the wearer.

A fourth prior art method is that taught by Wegener, U.S. Pat. No. 3,683,901, which utilizes a hollow cylindrical body having an enclosed extremity and a duct permitting communication between the inside of the hollow body, at a position adjacent to the closed end, and the outside. Additionally, the open end is provided with a circular constrictor which imparts pressure to restrict venus return similar to that above-described for other prior art devices. In the Wegener device, as the penis is inserted into the interior of the hollow body, air is forced out of the interior through the duct, forcing a one-way valve positioned therein to open. Unfortunately, once the penis has reached the duct opening then no further air can be removed since the penis occludes the duct. This leaves a cushion of air distal to the end of the penis, which will expand and contract with the pumping motion of the penis during sexual intercourse, producing the distracting sensation that the organ is going to come out of the device.

Further, the Wegener device assumes that the user must be able to achieve enough penis rigidity to drive the penis through the narrow area of the open end to produce any effective pressure change inside the hollow body and thereby actuate the valve to permit the penis to advance further. An impotent male with a flaccid penis cannot achieve insertion into the Wegener device, since insertion is achieved against a higher pressure of the compressed air in the interior of the device. Also, since the constrictor at the open end is to be tight enough to produce the goals listed above, a totally impotent male can never achieve enough of an erection to introduce the penis through the open end by pushing. Again, such constrictions, as noted before, if tight enough to produce corpora venous obstruction are also tight enough to produce harm to the skin and thereafter the viability of the penis.

Wegener further teaches incorporating a second duct with a one-way valve in the device with the second valve opening to admit air from the outside when too much negative pressure is present inside the hollow body. Indeed, if the user were able to get the device on, he would not be able to get it off if the second duct and valve were not present, and should the second valve fail, the only way to get the device off may be to cut if off at some risk to the enclosed penis.

In a further embodiment, Wegener shows a duct containing a pressure relief valve interposed in the enclosed end of the device, leading from the hollow body to the exterior at the front end thereof. The valve is said to release under pressure of ejaculation during intercourse and the duct will carry the ejaculate to the partner's cervix. However, as above-discussed, the pocket of air present in front of the penis would probably keep the valve from working and the ejaculate would remain in the hollow body and should any escape, the volume of the duct would hold some of the ejaculate thereby reducing the amount delivered to the cervix.

The present invention overcomes the deficiencies of the prior art by providing apparatus for simulating penile erection without injury or discomfort to the user.

SUMMARY OF THE INVENTION

The present invention provides a male penile device having a sleeve-like, hollow, cylindrical body simulating an erect penis formed of a soft, pliable, flexible material with one end enclosed to form a rounded portion and the remaining end open for allowing communication from the outside to the interior chamber formed within the body. The body has a thickened wall-section extending from the rounded, enclosed end toward the open end, with the wall-section reduced to a thin, flexible wall-section a preselected distance from and extending to the open end. A portion of a flexible small diameter tube is embedded in the thick wall-section, with one end of the tube opening into the interior chamber at the apex of the enclosed, rounded extremity most distal from the open end. The tube thereafter runs substantially lengthwise along the body of the device to emerge at the point of reduction from the thick wall-section to the thin wall-section. The remaining extremity of the tube extends freely from the point of emergence in the side wall.

With the thin wall-section rolled out and back, the distal end of the penis, after being properly lubricated, may be inserted through the open end into the interior chamber of the cylindrical body. When thus inserted, the sleeve-like body forms a seal around the glans penis head and a negative pressure may then be introduced into the interior chamber of the cylindrical body by drawing a vacuum through the flexible tube. As the negative pressure increases, the lubricated penis is drawn into the interior chamber and will continue to expand and lengthen until it reaches its anatomic limits or until it completely fills the chamber.

When the penis is in position, the small tube is clamped or plugged to prevent any reduction of the negative pressure in the interior chamber, thus eliminating any air pocket or cushion distal to the penis glans and the end of the device. The device may also contain a short length of tubing disposed in the most distal portion of the closed end of the device for allowing passage of male ejaculate. The ejaculate tube is of a substantially larger diameter than the evacuation tube to allow passage of the fluid ejaculate, although one projecting end of the tube collapses and occludes the tube when the vacuum is applied. Sexual intercourse can now be performed.

It is a feature of the present invention to provide a device for receiving and positioning the genital organ of an impotent male in a simulation of an erection for the purpose of performing sexual intercourse.

It is another feature of the present invention to provide a male penile device which can be used by an impotent male in comfort and safety.

It is still a further feature of the present invention to provide a male penile device for use by impotent males that utilizes a negative pressure to draw a flaccid penis into the device in response to a negative pressure introduced into the interior of the device.

These and other features and advantages of the present invention will become apparent from the following detailed description when considered in conjunction with the accompanying drawings.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the appended drawings, which drawings form a part of this specification. It is to be noted, however, that the appended drawings illustrate only typical embodiments of the invention and therefore are not to be considered limiting of its scope when the invention may admit to further equally effective embodiments.

In the drawings:

FIG. 1 is a longitudinal section or sagittal view of one embodiment of the male genital device of the present invention.

FIG. 2 is an end view of the device depicted in FIG. 1, looking into the interior chamber formed therein.

FIG. 3 is a longitudinal section or sagittal view of a second embodiment of the male genital device of the present invention.

FIG. 4 is an end view of the device depicted in FIG. 3, looking into the interior chamber formed therein.

FIG. 5 is a partial view in cross section of the thin wall portion of the device shown in FIG. 1, with the extremities of the opening positioned to receive the glans penis.

FIG. 6 is a side elevational view of an alternate embodiment of the device shown in FIG. 1, showing the interposition of circumferential thin wall sections along the length of the device to provide for biological erection of the penis.

FIG. 7 is a side elevational view of the device shown in FIG. 6, extended by biological erection.

FIG. 8 is a top plan view of the alternate embodiment of the device shown in FIG. 6, showing alternating thick and thin diamond-shaped areas used in place of the circumferential thin wall sections for permitting biological erection.

FIG. 9 is a longitudinal section or sagittal view of another alternate embodiment of the device shown in FIG. 1, including a hollow tubular structure fused to the enclosed extremity of the device to create an enclosed cavity for receiving a weighting material.

FIG. 10 is a longitudinal section or sagittal view of another embodiment of the device shown in FIG. 1, showing a loop formed on the closed extremity of the device.

DESCRIPTION OF THE PREFERRED EMBODIMENT

Referring now to FIGS. 1 and 2, the male genital device of the present invention includes a generally penile-shaped, sleeve-like, smooth walled, elastic, relatively soft and pliable hollow cylindrical body 10 with a closed distal end 12 and with an opposing open proximal end 14. An inner surface 16 of body 10 defines a substantially constant-diameter chamber 18 extending from distal end 12 lengthwise through the body 10 to communicate with the outside through opening 14 at the proximal end. Device 10 is formed with a relatively thick wall-section 21 between inner surface 16 and outer surface 20. Thick wall-section 21 extends from the most distal end 12 to a preselected location 26 which is in a spaced relation to proximal end 14. Further, distal end 12 includes rounded inner and outer wall surfaces 22 and 24, respectively, with the same preselected thickness as wall-section 21. At preselected location 26, spaced from proximal end 14, the outer diameter at surface 20 of device 10 is reduced to define a relatively thin wall-section 28 extending from location 26 to proximal end 14. In an actual device, thin wall-section 28 adjacent its extremity 14 will have a thickness ranging between 0.005 inches and 0.010 inches thus forming an extremely thin flexible end.

A flexible, small-diameter evacuation tube 38, having an outer diameter dimension less than the thickness of the thick wall-section of body 10, has a portion 40 embedded in thick wall-section 21 with an open end 42 communicating with interior 18 of device 10 at the most distal portion of interior rounded surface 22. The embedded portion of tube 38 enters the wall-section 21 proximate the beginning of thin wall-section 28, and extends substantially lengthwise along body 10 to the most distal extremity 12 where the end 42 of tube 38 communicates with the most distal part of interior wall 22, as above described. The remaining free end of tube 38 extends out of thick wall-section 21 for a purpose to be hereinafter further explained.

Referring now to FIGS. 3 and 4, the above-described device 10 has been modified by the addition of a short, thin walled, flexible ejaculate tube 43 interposed in distal end 12. Ejaculate tube 43 has a diameter substantially greater than that of tubing 38. One end 44 of tube 43 communicates with the interior 18 of device 10 through the most distal inner surface 22, with the other end 45 communicating to the exterior of device 10 through the most distal part of surface 24. End 45 projects out a short distance from end surface 24. The negative pressure applied to the interior chamber 18 of device 10 collapses the thin walled, flexible, ejaculate tube 43 flat against distal surface 24, thus occluding the opening of ejaculate tube 43 with a valve-like action of the collapsed tube.

In use, and referring now to FIGS. 1 through 5, the thin wall-section 28 adjacent the proximal extremity 14 is folded back upon itself as particularly shown in FIG. 5. The glans penis 70 of a flaccid penis 72, appropriately lubricated, is placed in the open rolled proximal end 15 of the device 10 and engages the interior surface 16. An appropriate suction or vacuum (negative pressure) is applied to the free extremity 51 of tube 38, which in turn creates a vacuum or negative pressure within the now sealed interior chamber 18 ahead of the glans penis 70. Such a negative pressure may be applied by any suitable means, like sucking on the end 51 of tube 38 by the wearer or by utilizing a suction device such as a syringe 75. If there is a distal ejaculation tube 43 formed in body 10, as shown in FIGS. 3 and 4, extremity 45 of the thin walled tube will collapse against itself and outer surface 24 as a result of the negative pressure created inside chamber 18 thus sealing chamber 18.

As the negative pressure increases, the lubricated, flaccid penis 72 will be drawn into the hollow interior 18 by the negative pressure and will continue to expand and lengthen until it reaches its anatomic limits, or until it completely fills the chamber 18 to its most distal end 22. As the penis fills the interior chamber 18, the importance of positioning the end 42 of evacuation tube 38 at the most distal point of surface 22 becomes apparent. Since the air is drawn out of chamber 18 ahead of the advancing glans penis 70, all the air will be evacuated prior to the distal end of the penis occluding the evacuation tube opening 42, as seen by the dotted outline of penis 72 and glans penis 70 in FIG. 1. Thus, there will be no air pocket distal to the end of the penis, or if the penis does not completely fill chamber 18, a negative pressure will exist in the remaining pocket of chamber 18, which will continue to exert an extending pressure on glans penis 70 rather than form a pocket or cushion of air ahead of the distal end of the penis.

It is important in practicing the invention that the device 10 be properly sized with respect to the wearing male's fully extended penis 72. The average erect penis size is 6.9 inches, and device 10 would usually be manufactured and available in several sizes, having both length and diameter variations. For example, devices 10 may be manufactured in three lengths, one size having a hollow interior 18 length of about 7.0-7.5 inches, one size 1-1½ inches shorter, and one size that is 1-1½ inches longer. Each length size may have a few diameter size variations also. The size of device 10 would be selected to fit the fully extended penis 72 as above described and shown in FIG. 1. Even if the device 10 is initially slightly longer than the extended penis 72, continued use of device 10 will naturally cause a small lengthening of penis 72 such that after a short interval of use, it will tend to fill all of the interior cavity 18 and occlude opening 42 of tubing 38 as shown in FIG. 1 and hereinabove described. If device 10 contains an ejaculate tube 43 as above described, and if the glans penis 70 occludes end 42 of tubing 38, the fluid ejaculate will be expelled through tube 43 by forcing the collapsed walls of end 45 open. However, even if the glans penis 70 does not occlude opening 42 of tubing 38, the substantially larger diameter of end 44 of tube 43 than tubing 38 will provide the fluid ejaculate with a lower pressure channel and hence the fluid ejaculate will be discharged through tubing 43 as above described, rather than be forced into the much smaller tubing 38.

When the penis is in proper position, the small tube 38 is clamped by a clamp 41 or plugged in any convenient manner to prevent air from returning to chamber 18 and interfering with the negative pressure created therein. For example, a small manually operated valve interposed in tube 38 may be used or a device similar to an IV tube clamp, such as is well known in the art, could be used. Thin wall-section 28 of proximal end 14 is then turned back to its original position so that section 28 now precisely surrounds the proximal shaft of the penis 72. This thin wall-section 28 functions as a valve, sealing the inside of the chamber 18 to the penis shaft 72. During sexual intercourse, as the penis 72 moves forward with device 10, the flexible end 28 permits comfortable flexing of proximal end 14 without breaking the seal to the interior of chamber 18. When the penis is moved rearward, the thin walled end 14 stretches about the penis shaft 72, insuring a tight seal. Since thin wall-section 28 has a thickness on the order of 0.005" to 0.010", and is made of an extremely flexible, soft material, any turgescence of the penis 72 can be accommodated by the thin wall-section 28 stretching, thereby accommodating the wearer with a precise, but comfortable, fit.

After thin wall-section 28 is repositioned, the free portion of tube 38 may be wrapped around body 10 adjacent the proximal end 14 so as to not interfere with the wearer during the use of the device. Any convenient method of restraining the free end of the wrapped tube 38 may be used. For example, the free end 51 may simply be tucked in under one of the tubing loops, or a simple cord clamp means 65 may be used. If the wearer is using device 10, shown in FIGS. 3 and 4, tube 43 will provide a means for the male ejaculate to be communicated to the exterior of device 10. The pressure of the ejaculate will be exerted against end 42 of the evacuation tubing 38 and against end 44 of tube 43, and be forced through tube 43 and the collapsed end 45 of tube 43 to the exterior of device 10 as hereinabove described.

Referring now to FIGS. 6 and 7, an alternate embodiment of device 10 is shown and is intended for use by a male who, while impotent at the beginning of an act of sexual intercourse, may during the act achieve partial or total biological erection. Accordingly, at preselected locations 46 along the length of device 10, the thick wall-section 21 is reduced in thickness to approximately the thickness of the thin wall-section 28 adjacent the proximal end 14. Each of the reduced thickness areas 46 is in the form of a narrow, circumferential band, each band extending over half the circumference of device 10. As shown in FIG. 7, if biological erection is achieved, the thin sections 46 will stretch to produce either an anterior or a posterior flexibility on the body 10, depending on the positioning of the device on the penis. This flexibility greatly aids in the comfort and safety of the user.

An alternate embodiment of the device shown in FIGS. 6 and 7 uses an alternating diamond pattern of thin wall-section dimensions as shown in FIG. 8. In this configuration, the thick wall-section 21 is again reduced to thin, flexible wall-sections 48, but in a diamond pattern which provides both greater anterior and posterior flexibility irrespective of the positioning of the device on the penis. In this embodiment, it will be necessary to embed the portion 40 of the small evacuation tube 38 through the thicker points of contact between the diamond-shaped thick walled sections. As above-mentioned, if during the act of sexual intercourse biological erection occurs, the reduced wall sections 48 will permit the device to extend, providing comfort and safety for the user.

The present invention is particularly adaptable, with suitable modifications, for the treatment of Peyronie's disease, which is an unnatural curvature in the penis caused by fibrous growth among other reasons. Additionally, the device as modified may also serve to aid in lengthening the penis, if this is desired. As both of these require the device to be worn for extended periods, it can be seen that the prior art devices which use high circumferential pressure on the proximal end of the penis cannot be used because of the health risk of altering the vascular dynamics of the penis.

Referring now to FIG. 9, modification to the basic device 10 is shown to include an extension 50 of thick-walled section 21 beyond the rounded portion 12 of the distal extremity 24. The extended wall-section 50 has approximately the same wall thickness dimension as thick wall-section 21. Wall section 50 is formed with a closed, curved distal end 52 which defines an enclosed cavity or chamber 54 at the distal extremity 24 of device 10. The enclosed cavity 54 is then filled with a suitable weighting material having a high weight-to-volume ratio. Such a weighting material may conveniently be mercury.

In use, the device 10 is attached to the penis in the normal manner as has been above-described. The weight of the material placed in cavity 54 results in a straightening and lengthening force being exerted on the user's penile organ. However, as continuous use of the device is required to obtain noticeable results, the device is designed to be worn during an entire day to aid in either straightening or lengthening the penis, whichever produces the desired result.

It becomes apparent, however, that the device shown in FIG. 9 is not suitable for use at night while the user is asleep. Accordingly, and referring now to FIG. 10, another modification to device 10 is shown in which a loop or ring 60 is formed on the surface 24 of distal extremity 12. In use, one end of a cord or cable (not shown) is attached to the loop 60 in any convenient manner, with the remaining end of the cord attached to a pulley and weight arrangement (not shown) to provide the necessary force for stretching the penis while the wearer is asleep. Although not shown, it may be advantageous to reinforce the ring with a metal insert or other suitable strengthening device.

Another advantage of the device 10 as disclosed herein is its simplicity and ease of cleaning. After removal of device 10 from penis 72, the interior chamber 18 and the exterior surface 20 can be easily cleaned and sterilized. Similarly, the open tubes 38 and 43 can be cleaned and sterilized by pumping or forcing an appropriate cleanser through the tubing by any suitable means, such as a hand pump or syringe (not shown). Thus, device 10 can be utilized indefinitely if proper care is taken of the device. This is in contrast to prior art devices using enclosed valves, which may malfunction and tend to trap ejaculate and other materials, thus making it difficult to achieve proper hygiene and sterilization.

Although specific embodiments have been described in detail hereinbefore, it is understood that the subject invention is not limited thereto, and all variations and modifications thereof are contemplated and are included within the spirit and scope of the invention as defined by the appended claims.

What is claimed is:

1. A device for treating male impotence, comprising a substantially cylindrical hollow body made of a flexible and elastic material, said body having a distal closed end and a proximal open end, said open end terminating in a thin flexible sleeve-like portion that can be rolled up over said thick-walled body portion to permit the distal end of a male penis to engage the inner walls of said hollow body, said thin flexible sleeve-like portion further functioning as a seal about the male penis when returned to its unrolled condition, and
a length of flexible tubing at least a portion of which is disposed longitudinally in the wall of said body, one end of said tubing communicating with the most distal end of the interior of said hollow body, the other end of said tubing freely extending from said body for permitting the evacuation of the air in the interior of said hollow body forward of said engaged male penis for exerting a vacuum therein for drawing said male penis to its anatomic limit into the interior of said hollow body.

2. The device as described in claim 1, further including a short thin-walled flexible length of tubing disposed in the most distal portion of said closed end of said hollow body, one end of said tubing communicating with the most distal end of the interior of said hollow body adjacent said one end of said length of flexible tubing disposed in the walls of said body, the other end of said short tubing projecting distally of the closed end of said hollow body for permitting said projecting thin-walled flexible tubing to collapse in response to said vacuum exerted interiorly of said hollow body for occluding the opening in said short length of tubing when said vacuum is applied, but permitting passage of fluid ejaculate in response to pressure exerted by male ejaculation during intercourse.

3. The device as described in claim 1 or 2, wherein said walls of said hollow body have disposed therein generally peripheral thin-walled sections for permitting limited longitudinal flexibility and expansion of said hollow body in response to partial or total biological erection of said male penis after insertion into said hollow body.

4. The device as described in claim 1, further including a rounded extension portion distally disposed and attached to the exterior distal closed end of said hollow body, said rounded extension having disposed therein a closed cavity containing a selected weighting material.

5. The device as described in claim 4, wherein said selected weighting material is mercury.

6. The device as described in claim 1, further including an enlarged ring distally disposed and attached to the exterior closed end of said hollow body for attaching a weight for applying a force longitudinally to said hollow body and enclosed penis.

7. The device described in claim 1 or 2, further including
evacuation means adapted to sealingly engage said free end of said length of flexible tubing for permitting the evacuation of the air in the interior of said hollow body, and
means for selectively opening or closing said length of extending flexible tubing intermediate said free end and said point of extension of said tubing from said hollow body for sealingly closing said tubing when said desired vacuum has been effected and permitting disengagement of said evacuation means, and for opening said tubing to eliminate said vacuum in the interior of said hollow body.

8. The device as described in claim 7, further including retaining means attached to said extending length of flexible tubing adjacent its free end for providing a means of retaining said free end adjacent said hollow body during use.

9. A kit to provide an external device for treating male impotence, comprising a prosthetic device comprising a substantially cylindrical hollow body made of a flexible and elastic material, said body having a distal closed end and a proximal open end, said open end terminating in a thin flexible sleeve-like portion that can be rolled up over said thick-walled body portion to permit the distal end of a male penis to engage the inner walls of said hollow body, said thin flexible sleeve-like portion further functioning as a seal about the male penis when returned to its unrolled condition, and a length of flexible tubing at least a portion of which is disposed longitudinally in the wall of said body, one end of said tubing communicating with the most distal end of the interior of said hollow body, the other end of said tubing freely extending from said body for permitting the evacuation of the air in the interior of said hollow body forward of said engaged male penis for exerting a vacuum therein for drawing said male penis to its anatomic limit into the interior of said hollow body, evacuation means adapted to sealingly engage said free end of said length of flexible tubing for permitting the evacuation of the air in the interior of said hollow body, and means for selectively opening and closing said length of extending flexible tubing intermediate said free end and said point of extension of said tubing from said hollow body for sealingly closing said tubing when said desired vacuum has been effected and permitting disengagement of said evacuation means, and for opening said tubing to eliminate said vacuum in the interior of said hollow body.

10. The prosthetic device as described in claim 9, further including a short thin-walled flexible length of tubing disposed in the most distal portion of said closed end of said hollow body, one end of said tubing communicating with the most distal end of the interior of said hollow body adjacent said one end of said length of flexible tubing disposed in the walls of said body, the other end of said short tubing projecting distally of the closed end of said hollow body for permitting said projecting thin-walled flexible tubing to collapse in response to said vacuum exerted interiorly of said hollow body for occluding the opening in said short length of tubing when said vacuum is applied, but permitting passage of fluid ejaculate in response to pressure exerted by male ejaculation during intercourse.

11. The device as described in claim 9 or 10, wherein said walls of said hollow body have disposed therein generally peripheral thin-walled sections for permitting limited longitudinal flexibility and expansion of said hollow body in response to partial or total biological erection of said male penis after insertion into said hollow body.

12. The prosthetic device as described in claim 9 or 10, further including retaining means attached to said extending length of flexible tubing adjacent its free end for providing a means of retaining said free end adjacent said hollow body during use.

* * * * *

UNITED STATES PATENT OFFICE
CERTIFICATE OF CORRECTION

Patent No. 4,175,554     Dated November 27, 1979

Inventor(s)  Frank J. Gerow

It is certified that error appears in the above-identified patent and that said Letters Patent are hereby corrected as shown below:

[54] PROSTHESIS FOR MALE IMPOTENCE

[76] Inventor: Frank J. Gerow, 12702 Barryknoll, Houston, Texas 77024

Signed and Sealed this

Seventh Day of April 1981

[SEAL]

Attest:

RENE D. TEGTMEYER

Attesting Officer     Acting Commissioner of Patents and Trademarks